(12) United States Patent
Vartuli et al.

(10) Patent No.: US 7,720,321 B2
(45) Date of Patent: May 18, 2010

(54) FIBER OPTIC SENSOR AND METHOD FOR MAKING

(75) Inventors: James Scott Vartuli, Rexford, NY (US); Kenneth Sherwood Bousman, Albany, NY (US); Kung-Li Deng, Waterford, NY (US); Kevin Paul McEvoy, Ballston Spa, NY (US); Hua Xia, Altamont, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/780,701

(22) Filed: Jul. 20, 2007

(65) Prior Publication Data

US 2009/0022449 A1 Jan. 22, 2009

(51) Int. Cl.
*G02B 6/00* (2006.01)

(52) U.S. Cl. .......................................................... 385/12

(58) Field of Classification Search ........................ None
See application file for complete search history.

(56) References Cited

U.S. PATENT DOCUMENTS

| | | | |
|---|---|---|---|
| 5,280,172 A | | 1/1994 | Di Bin et al. |
| 5,457,313 A | | 10/1995 | Baylor et al. |
| 5,496,997 A | * | 3/1996 | Pope ..................... 250/227.21 |
| 5,674,751 A | * | 10/1997 | Jaduszliwer et al. ........ 436/116 |
| 5,864,641 A | | 1/1999 | Murphy et al. |
| 5,900,215 A | | 5/1999 | Seifert et al. |
| 6,445,861 B1 | | 9/2002 | Shaw |
| 7,058,243 B2 | | 6/2006 | Tao et al. |
| 7,151,872 B1 | | 12/2006 | Xia et al. |
| 7,228,017 B2 | | 6/2007 | Xia et al. |
| 2004/0264901 A1 | * | 12/2004 | Tao et al. ..................... 385/128 |
| 2006/0008677 A1 | | 1/2006 | Bewlay et al. |
| 2006/0215959 A1 | | 9/2006 | McCarthy et al. |
| 2006/0222762 A1 | | 10/2006 | McEvoy et al. |

OTHER PUBLICATIONS

Schweizer-Berberich et al.; The effect of Pt and Pd surface doping on the response of nanocrystalline tin dioxide gas sensors to CO; Sensors and Actuators; 1996, pp. 71-75, Elsevier Science S.A.

Wang et al.; Low-temperature carbon monoxide gas sensors based gold/tin dioxide; Science Direct; Oct. 3, 2006; pp. 1728-1731; Solid-State Electronics 50 (2006); Elsevier Ltd.

Boulahouache et al.; Oxidation of carbon monoxide on platinum-tin dioxide catalysts at low temperatures; Applied Catalyst; 1992; pp. 115-123; Elsevier Science Publishers B.V.

Bevenot et al.; Surface plasmon resonance hydrogen sensor using an optical fibre; Measurement Science and Technology; pp, 118-124; 13 (2002); Institute of Physics Publishing.

Mac Craith B.D. et al. "Led-Based Fibre Optic Oxygen Sensor Using Sol-gel Coating" Electronics Letters. IEE Stevenage, GB, vol. 30 No. 11, May 26, 1994 pp. 888-889 p. 888, col. 2, line 10-line 21; figure 1, p. 888, col. 2, line 23-line 24, p. 888, col. 2, line 27-line 33.

(Continued)

*Primary Examiner*—Sung H Pak (57) ABSTRACT

A fiber optic sensor including a fiber having a modified surface integral with the fiber wherein the modified surface includes an open pore network with optical agents dispersed within the open pores of the open pore network. Methods for preparing the fiber optic sensor are also provided. The fiber optic sensors can withstand high temperatures and harsh environments.

28 Claims, 8 Drawing Sheets

OTHER PUBLICATIONS

Hua Xia et al. "Temperature-dependent Fiber Optic Hydrogen Gas Sensor Response Characteristics" Proceedings of the SPIE—The International Society for Optical Engineering - Photorefractive Fiber and Crystal Devices: Materials, Optical Properties, and Applications XII, vol. 6314, Aug. 16, 2006 pp. 631411-1-631411-7 paragraph—Experiments, abstract.

EP Search Report Issued in EP Application No. 08156110.2 issued on Dec. 1, 2008.

* cited by examiner

FIBER OPTIC SENSOR AND METHOD FOR MAKING

STATEMENT REGARDING FEDERALLY SPONSORED RESEARCH & DEVELOPMENT

This invention was made with Government support under contract number DE-FC26-05NT42438 awarded by the United States Department of Energy. The Government has certain rights in the invention.

FIELD OF THE INVENTION

This invention relates to a method for making a fiber optic sensor and more particularly, for a fiber optic sensor for harsh environments.

BACKGROUND OF THE INVENTION

Fiber optic sensors may be used to monitor dynamic chemical and physical processes that are associated with changes in an environment. A typical fiber optic sensor positions a sensor material, with the assistance of one or more types of support, to interact with the substance or environment that is being monitored, measured and/or detected. A chemical fiber optic sensor contains an optical agent that identifies optical index changes based upon unique chemical environments. To function properly, the optical agent must be in an optically clear support structure that holds the optical agent and permits the optical agent to interact with the environment or substance being monitored, measured or detected.

Conventional fiber optic sensors are often limited to relatively mild temperature conditions and begin to break down when employed in high temperature and/or harsh environments such as, gas or steam turbine exhausts, coal-fired boilers and aircraft engines.

U.S. Pat. No. 5,496,997 to Pope, discloses an optical fiber where the distal end of the fiber is coupled to amorphous silica microspheres by an adhesive material. The sensor can fail in harsh environments, as the adhesive layer may break down at high temperatures or in the harsh environments.

What is needed is a fiber optic sensor that can withstand high temperatures and harsh environments.

SUMMARY OF THE INVENTION

In one embodiment, a fiber optic sensor comprises a fiber having a modified surface integral with the fiber, said modified surface comprising an open pore network and optical agents disposed within the open pores of the open pore network.

In another embodiment, a process for making a fiber optic sensor comprises applying ceramic material to a fiber and forming an open pore network structure, dispersing optical agents within the pores of the open pore network and integrating the ceramic material with the fiber.

In another embodiment, a process for making a fiber optic sensor comprises applying a ceramic material mixture comprising ceramic material and optical agents to a fiber, forming an open pore network structure within the ceramic material and integrating the ceramic material with the fiber.

The various embodiments provide fiber optic sensors that can withstand high temperatures and harsh environments.

DETAILED DESCRIPTION OF THE INVENTION

The singular forms "a," "an" and "the" include plural referents unless the context clearly dictates otherwise. The endpoints of all ranges reciting the same characteristic are independently combinable and inclusive of the recited endpoint. All references are incorporated herein by reference.

The modifier "about" used in connection with a quantity is inclusive of the stated value and has the meaning dictated by the context (e.g., includes the tolerance ranges associated with measurement of the particular quantity).

"Optional" or "optionally" means that the subsequently described event or circumstance may or may not occur, or that the subsequently identified material may or may not be present, and that the description includes instances where the event or circumstance occurs or where the material is present, and instances where the event or circumstance does not occur or the material is not present.

In one embodiment, a fiber optic sensor comprises a fiber having a modified surface integral with the fiber, said modified surface comprising an open pore network and optical agents disposed within the open pores of the open pore network.

A fiber optic sensor may be used to measure physical, electrical and chemical parameters. In one embodiment, the fiber optic sensor is a chemical fiber optic sensor.

A fiber comprises a fiber core and optionally, a fiber cladding. The fiber cladding, if present, at least partly surrounds the fiber core, which forms a waveguide that extends longitudinally along an axis and includes parts having variations in refractive index (or optical thickness) to form an optical diffraction grating.

The fiber core is transparent and may comprise sapphire, a porous sol-gel glass or a fused silica material.

The fiber cladding may be transparent and may be made of the same material as the core, but with a low refractive index. In one embodiment, the fiber cladding comprises glass or silica.

At least a portion of a surface of the fiber is modified. The modified surface may be on the fiber core or the fiber cladding, if present, of the fiber. The modification to the fiber comprises applying a ceramic material to the surface of the fiber in any conventional manner. As the ceramic material solidifies, it forms a porous and optically clear support structure, which is a three-dimensional matrix or lattice type structure with a plurality of interconnecting pores that extend completely throughout the support structure and create an open pore network.

The pore sizes may be any size suitable for allowing a sensing gas to pass through the support structure. In one embodiment, the pore sizes are up to about 150 nm in diameter. In another embodiment, the pores sizes are from about 1 nm to about 150 nm in diameter. The pore sizes may be controlled in a conventional manner by adjusting the time and temperature while the material is solidifying.

In one embodiment, the ceramic material is applied by spraying, brushing, rolling, pouring, dipping, immersing coating or applying a film to a surface of the fiber. In one embodiment, a surface of the fiber is modified by coating the surface. In another embodiment, a surface is modified by dipping the fiber. In another embodiment, a surface is modified by forming a film on the surface.

The ceramic material may be silica, alumina or titania. The alumina, titania and silica may be derived from an organo-metallic, such as a tetraethoxyorthosilicate. In one embodiment, the ceramic material comprises silica.

Optical agents are sensors that chemically sense unique chemical environments and measure the optical index of the fiber cladding. Optical agents may be any type of sensor that is known in the art. In one embodiment, the optical agents may be metals or transition metals. In one embodiment, the transition metal is any compound comprising Group 8-10 transition metals, such as ruthenium, rhodium, platinum and palladium. In one embodiment, the optical agent is palladium. In another embodiment, the optical agent may include a metal oxide. In another embodiment, the metal oxide may include tin dioxide, yttrium oxide, vanadium oxide, titanium oxide and tungsten oxide.

The optical agents are disposed within the open pores of the open pore network and are at least partially exposed to the ambient air. Optical agents are disposed into the open pores by dispersing the optical agents into the open pore network by any conventional method. The optical agents may be dispersed by spraying, brushing, rolling, pouring, dipping, immersing or coating the modified surface with the optical agents. In one embodiment, the optical agents are dispersed within the pores of the open pore network by dipping the modified fiber optic into a solution comprising optical agents. The solution may be prepared by blending optical agents with water or alcohol. The ceramic material is integrated with the fiber by intimately bonding the ceramic material to a fiber surface without the need for adhesive materials or adhesive layers. The ceramic material infiltrates the surface of the fiber to form an integrated and modified surface on the fiber that effectively replaces the fiber surface with the new modified surface. The ceramic material may be integrated with the fiber by any means suitable for densifying and intimately bonding the ceramic material to a fiber surface. The densified ceramic material forms an open pore network within a dense structure that holds the optical agents in place and provides access to the environment or substance that is to be measured, monitored or detected. This open pore network holds and protects the optical agents in a support structure that is thermally, chemically and mechanically robust and stable.

In one embodiment, the ceramic material may be densified and bonded to the fiber by heat treatment, drying or irradiation. In another embodiment, the ceramic material is heat treated. Heat treatment may be made in any conventional manner. In one embodiment, the modified fiber is heated between about 300° C. and about 600° C. for up to about 4 hours. In one embodiment, the modified fiber is heated for about 1 to about 3 hours. Continued heating at higher temperatures or for longer times will eventually cause the open pore network to become fully dense having little or no porosity.

In another embodiment, a process for making a fiber optic sensor comprises applying ceramic material to a fiber to form an open pore network structure, dispersing optical agents within the pores of the open pore network and integrating the ceramic material with the fiber.

As stated above, the ceramic material may be silica, alumina or titania. The alumina, titania and silica may be derived from an organo-metallic, such as a tetraethoxyorthosilicate.

In one embodiment, the ceramic material comprises spherical particles having diameters in a range from about 20 nm to about 700 nm. The diameters are measured by a scanning electron microscope. In one embodiment, the spherical particles are monosized. In another embodiment, at least about 95% of the spherical particles are within about 10% of the mean diameter of the spherical particles.

In another embodiment, the ceramic material comprises spherical particles of silica. Spherical particles of silica may be made by adding a silica precursor, such as tetraethoxyorthosilicate, into a solution comprising alcohol and optionally, water from about 1 to about 50 percent by weight ammonia. The size of the particles is controlled by the relative concentrations of water, ammonia and alcohol. In one embodiment, the alcohol is ethanol. The amount of alcohol is in the range of from about 10 to about 70 percent by weight based on the weight of the solution. The amount of ammonia is present from about 1 to about 50 percent by weight based on the weight of the solution. The amount of water is present from about 10 to about 70 percent by weight based on the weight of the solution. The amount of silica precursor is present from about 1 to about 10 percent by weight based on the weight of the solution.

In one embodiment, the ceramic material comprising spherical particles is applied by spraying, brushing, rolling, pouring, dipping, immersing coating or applying a film to a surface of the fiber. In one embodiment, a surface of the fiber is modified by dipping the fiber into an aqueous solution of ceramic spherical particles. The spherical particles adhere to the surface of the fiber through van der Waals forces. As the water from the solution dries, capillary forces from the evaporating water film pull the spherical particles into a dense network of touching particles and open spaces forming open pores.

The optical agents are dispersed within the open pores of the open pore network by any conventional method. As stated above, the optical agents may be dispersed by spraying, brushing, rolling, pouring, dipping, immersing or coating the modified surface with the optical agents. In one embodiment, the optical agent is dispersed within the open pore network by solution. The optical agents are added to a solution comprising water or alcohol and the fiber with the modified surface is dipped into the solution. Repeated steps of dispersing the optical agent into the open pore network may be used to increase the concentration of the optical agents on the fiber. The optical agents are situated within the open pores of the open pore network and are at least partially exposed to the environment or substance to be measured.

The ceramic material is integrated with a fiber surface by any means suitable for densifying and intimately bonding the ceramic material to the fiber without the need for adhesive materials or adhesive layers.

Figure 1A:
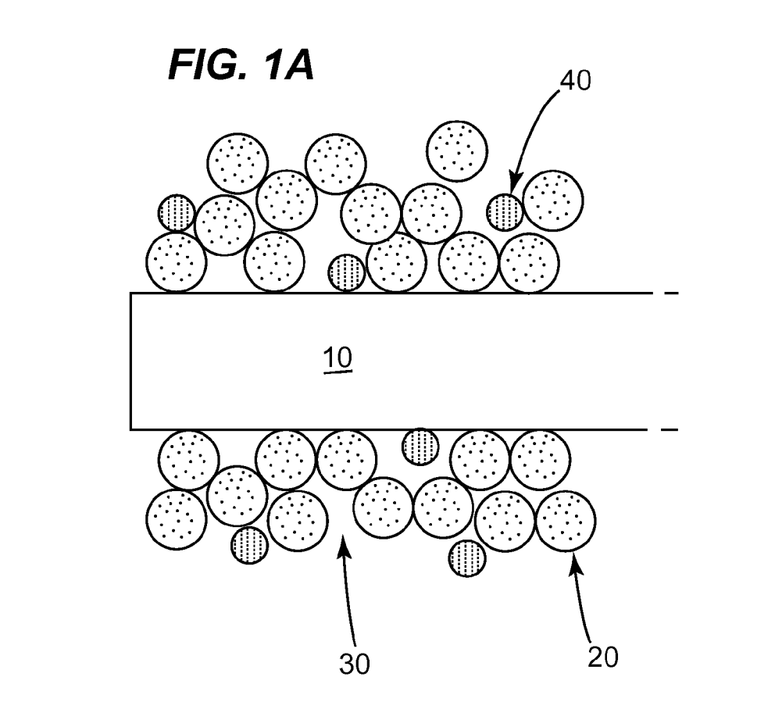
FIG. 1A is a diagram depicting a modified surface on a fiber before heat treatment.
Figure 1B:
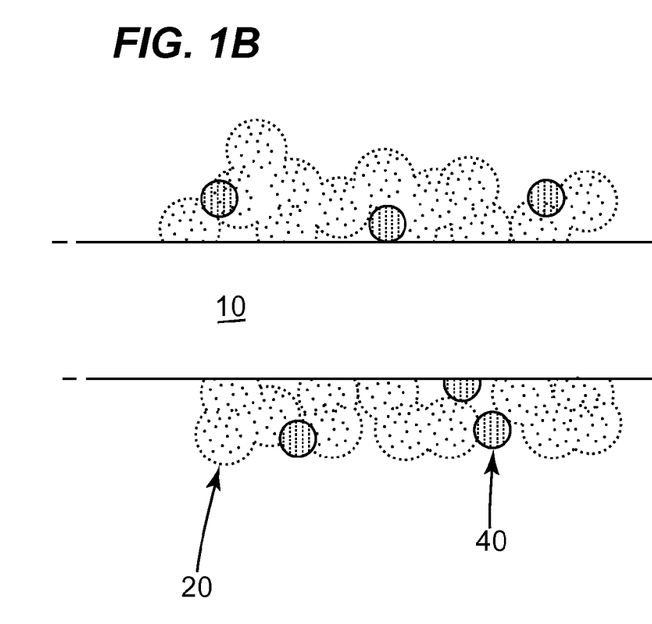
FIG. 1B is a diagram depicting a modified surface on a fiber after heat treatment.

FIG. 1A is a diagram depicting a fiber 10 before heat treatment. The surface of the fiber 10 is modified by the application of a ceramic material 20 comprising ceramic spherical particles. The ceramic particles 20 adhere to the surface of the fiber 10 and form an open pore network of touching particles and open spaces 30. Optical agents 40 are dispersed within the open pores 30 of the open pore network. FIG. 1B is a diagram depicting the fiber optic 10 after heat treatment. During heat treatment, the ceramic spherical particles 20 densify and integrate with the fiber 10 to form an open pore network within a dense ceramic material 20. The optical agents 40 are supported and held in place by the open pore network in the ceramic material 20 and are exposed to the environment or substance to be measured.

In another embodiment, a process for making a fiber optic sensor comprises applying a ceramic material mixture comprising ceramic material and optical agents to a fiber, forming an open pore network structure within the ceramic material and integrating the ceramic material with the fiber.

The ceramic material mixture comprises ceramic material and optical agents. The ceramic material mixture is prepared by adding optical agents to the ceramic material. The optical agents may be blended with the ceramic material in any conventional manner. In one embodiment, the optical agents and ceramic material are blended together in solution. In another embodiment, a solution of tetraethoxyorthosilicate, alcohol and optical agents is prepared.

The ceramic material mixture is applied to a fiber surface in any conventional manner. In one embodiment, the ceramic material is applied by spraying, brushing, rolling, pouring, dipping, immersing coating or applying a film to the surface. In one embodiment, the ceramic material mixture is applied by coating the surface of the fiber. In another embodiment, the ceramic material mixture is applied by dipping the fiber. In another embodiment, a film comprising the ceramic material mixture is formed on the surface of the fiber.

The open pore network may be formed by any suitable means for hardening ceramic material, such as drying or heat treating. As the ceramic material dries or is heated, the ceramic material begins to gel and cracks begin to form in the ceramic material. The cracks provide an open pore network within the dense ceramic material. The amount of cracking can be controlled by the rate of change of humidity and by the heat or drying rate.

The ceramic material is integrated with the fiber optic by any means suitable for densifying and intimately bonding the ceramic material to the fiber without the need for adhesive materials or adhesive layers.

In another embodiment, the ceramic material mixture further comprises a polymer. The polymer may be any type of organic polymer that will decompose at elevated temperatures, such as during a heat treatment step. In one embodiment, the organic polymer may be oxides of polyolefins, latex polymers, polyesters and polypropylenes. In another embodiment, the organic polymer includes polyethylene oxide or polypropylene oxide. The polymer may be added to the ceramic material in an amount of from about 0.1 to about 10 percent by volume based on the ceramic material.

The polymer aids in producing an open pore network within a dense ceramic material by causing cracks and voids to form in the ceramic coating. The ceramic material is heat treated in any conventional manner and the polymer will decompose during the heat treating step and leave voids in the coating, which will increase the open pores within the dense ceramic coating. The voids and cracks within the ceramic coating are large enough to allow gas to diffuse through the voids, but are small enough to not cause structural damage to the ceramic coating. In one embodiment, the voids may be from about 10µ in diameter to about 100µ in diameter.

Figure 2A:
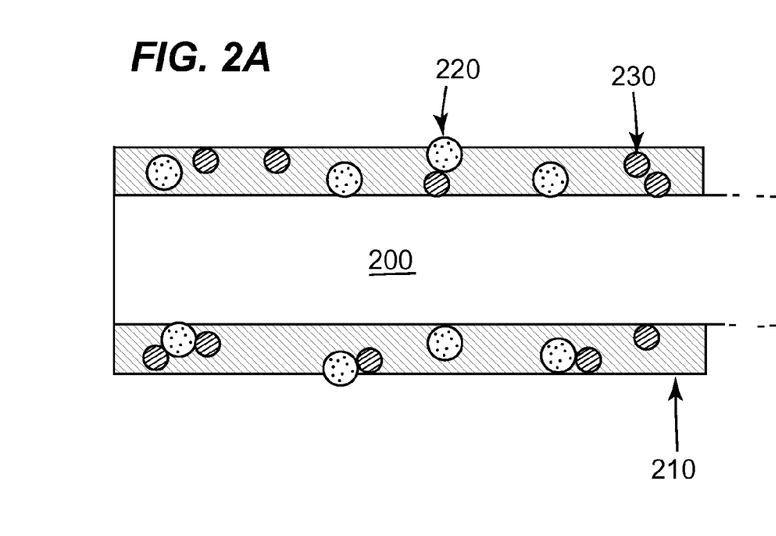
FIG. 2A is a diagram depicting a modified surface on a fiber before heat treatment.
Figure 2B:
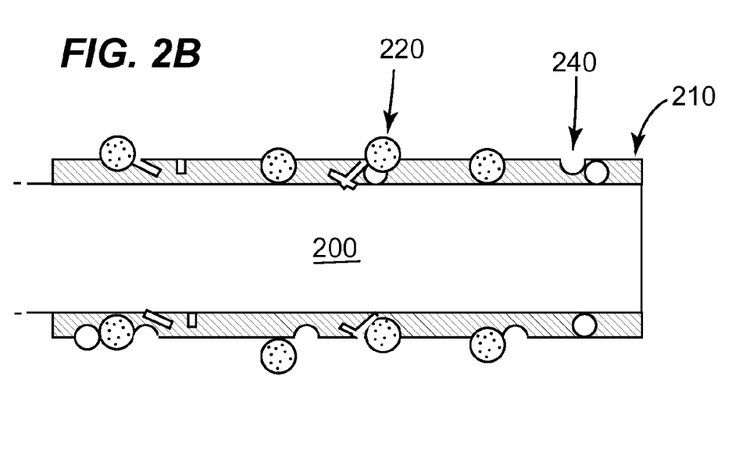
FIG. 2B is a diagram depicting a modified surface on a fiber after heat treatment.
Figure 3:
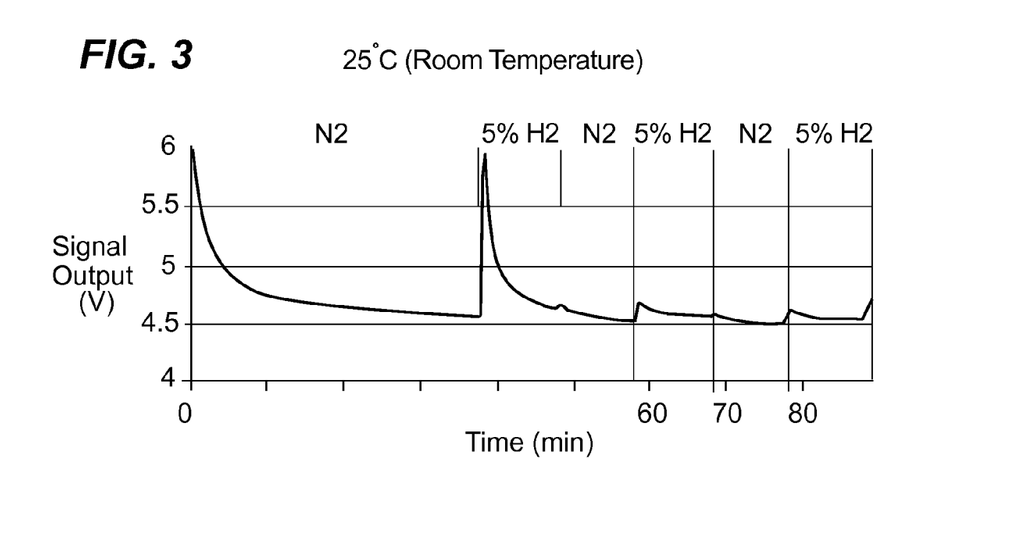
FIG. 3 is a graph showing the $H_2$ response optical reflection curve between alternating 5% $H_2$ in $N_2$ gas at 25° C. (room temperature). The graph is signal output in volts vs. time in minutes.
Figure 4:
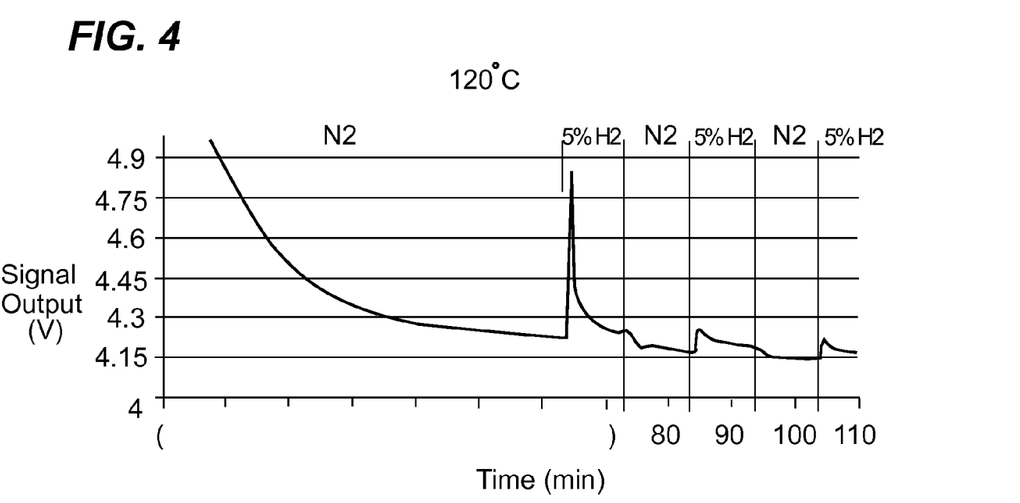
FIG. 4 is a graph showing the $H_2$ response optical reflection curve between alternating 5% $H_2$ in $N_2$ gas at 120° C. The graph is signal output in volts vs. time in minutes.
Figure 5:
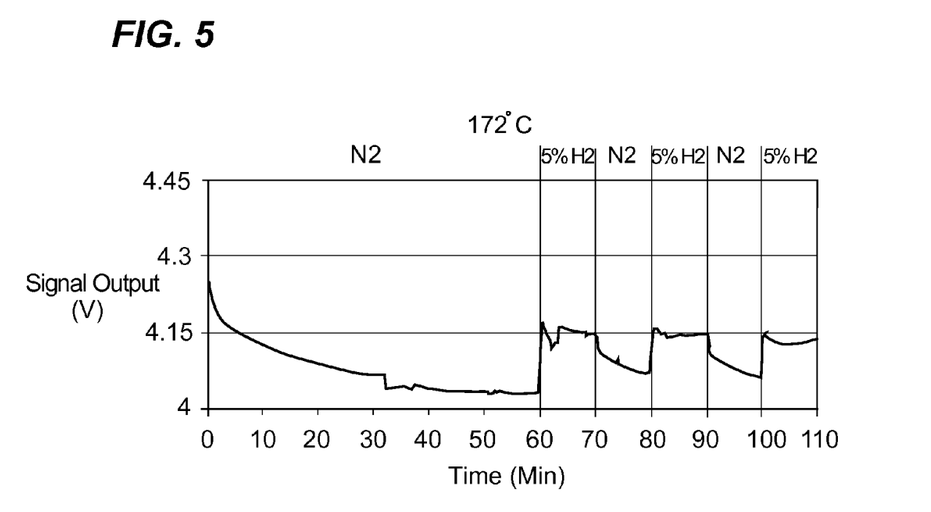
FIG. 5 is a graph showing the $H_2$ response optical reflection curve between alternating 5% $H_2$ in $N_2$ gas at 172° C. The graph is signal output in volts vs. time in minutes.
Figure 6:
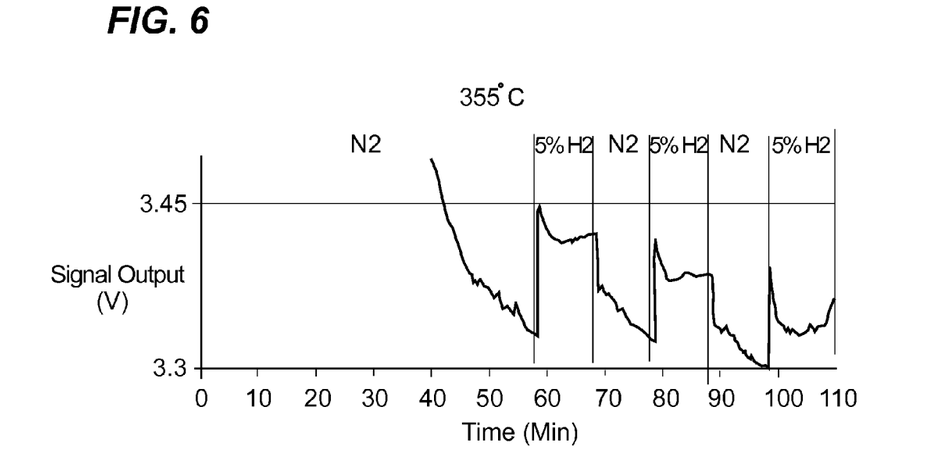
FIG. 6 is a graph showing the $H_2$ response optical reflection curve between alternating 5% $H_2$ in $N_2$ gas at 355° C. The graph is signal output in volts vs. time in minutes.
Figure 7:
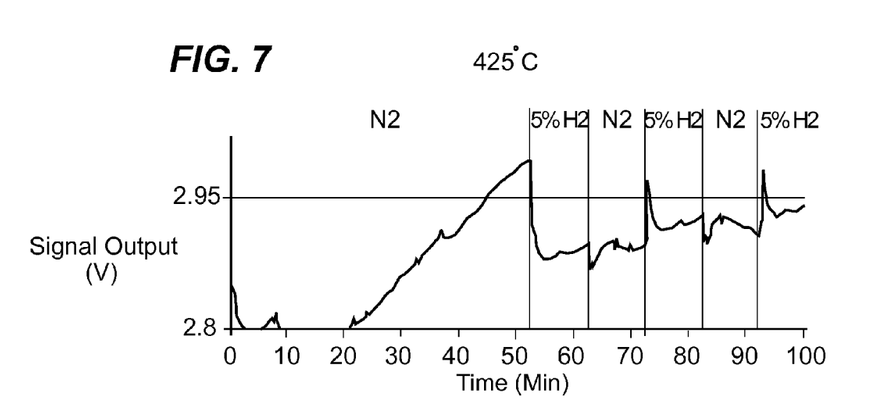
FIG. 7 is a graph showing the $H_2$ response optical reflection curve between alternating 5% $H_2$ in $N_2$ gas at 425° C. The graph is signal output in volts vs. time in minutes.
Figure 8:
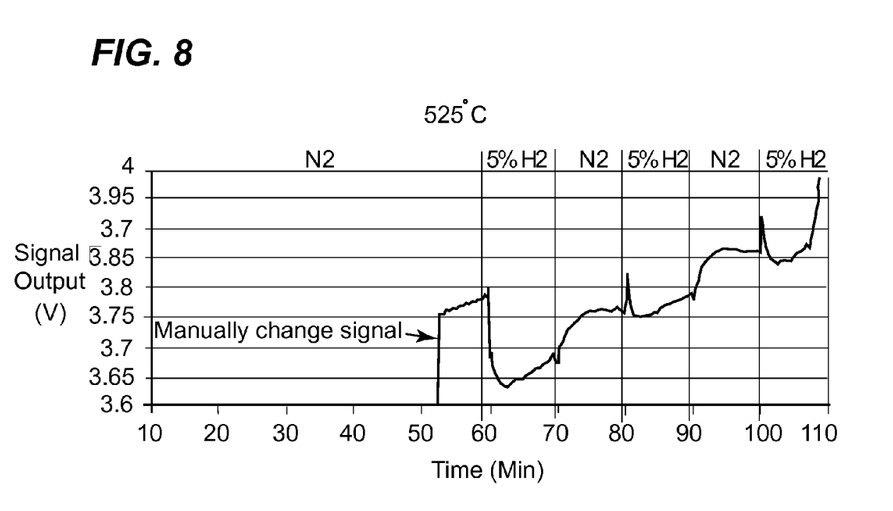
FIG. 8 is a graph showing the $H_2$ response optical reflection curve between alternating 5% $H_2$ in $N_2$ gas at 525° C. The graph is signal output in volts vs. time in minutes.

FIG. 2A is a diagram depicting a fiber 200 before heat treatment. A mixture of a ceramic material 210, optical agents 220 and a polymer 230 are applied to the surface of a fiber 200 and allowed to dry under a controlled humidity to induce cracking (not shown) in the dense ceramic material. FIG. 2B is a diagram depicting a fiber 200 after heat treatment. The modified surface is heat treated and during heat treatment, the ceramic material 210 densifies and intimately bonds with the fiber optic 200. The polymer 230 decomposes leaving voids 240 in the ceramic material 210. The optical agents 220 are supported and held in place within the open pore network formed within the ceramic material 210 and are exposed to the environment or substance to be measured.

In order that those skilled in the art will be better able to practice the present disclosure, the following examples are given by way of illustration and not by way of limitation.

EXAMPLES

Example 1

A mixture of 89.5 percent by weight tetraethoxyorthosilicate, 10.5 percent by weight palladium and 40 percent by weight based on the weight of the tetraethoxyorthosilicate and palladium of 1-propanol was prepared. A silica, having spherical particles with an average diameter of 300 nm where 95% of the particles have a diameter within 10% of the average diameter, was formed from the tetraethoxyorthosilicate and 1-propanol.

A film of the mixture of silica and palladium was applied to a glass substrate and heat treated at 400° C. for 2 hours. The film thickness was about 100 µm.

The fiber optic sensor was tested for hydrogen responses between room temperature and 525° C. FIGS. 3-8 show the $H_2$ response optical reflection curve between alternating 5% $H_2$ in $N_2$ gas at 25° C. (room temperature), 120° C., 172° C., 355° C., 425° C. and 525° C., respectively. The sensor measured $H_2$ sensing up to about 355° C.

Figure 9:
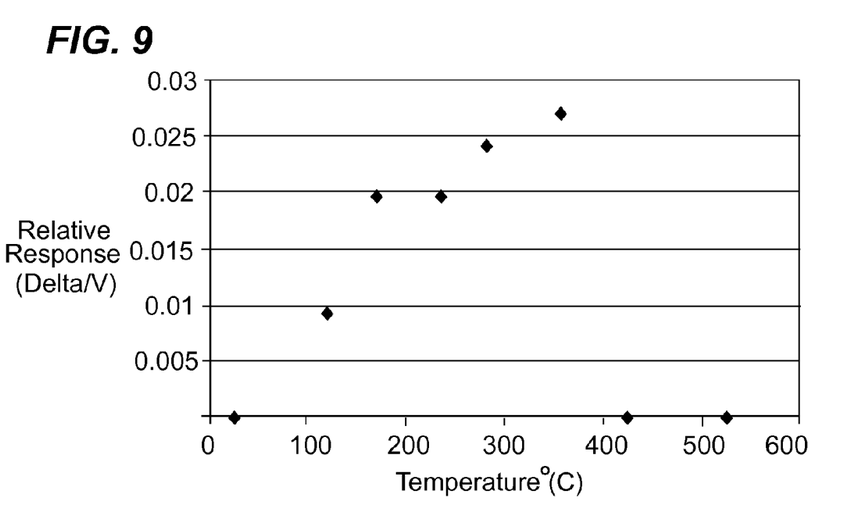
FIG. 9 is a graph showing the summarized relative response to the $H_2$ gas. The graph is relative response (Delta/V) vs. temperature (° C.).

The relative response to the $H_2$ gas is summarized in FIG. 9. The relative response, which is the quotient of the change of signal to the signal level. The values are evaluated by the average using the faster change signal. The results show that in the temperature range where the film is capable of sensing, sensitivity increases with increasing temperatures.

Figure 10:
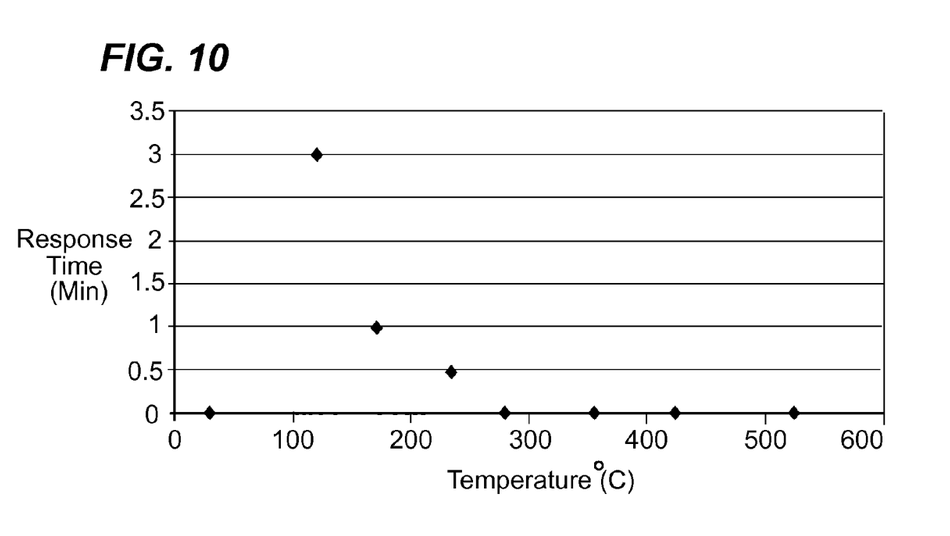
FIG. 10 is a graph showing the response time in minutes vs. temperature in ° C.

FIG. 10 is the response time over temperature. The response time values are evaluated by an average using the faster change signal. The results show that within the temperature where the film is capable of sensing, the higher the temperature, the shorter the response time, which corresponds to the increasing chemical reaction rate at the elevated temperature.

Prior art Pd-alloy based sensing materials interact with hydrogen at room temperature allowing the detection and measurement of hydrogen by optical and fiberoptic techniques, but do not show detection at higher temperatures. Ref. X Bévenot, A Trouillet, C Veillas, H Gagnaire, and M. Clément, Meas. Sci. Technol. 13, 118-124 (2002).

Example 2

A mixture of 80 percent by weight tetraethoxyorthosilicate, 15 percent by weight tin dioxide, 5 percent by weight palladium and 8 percent by weight based on the weight of the tetraethoxyorthosilicate, palladium and tin dioxide of 1-propanol was prepared. A silica, having spherical particles with an average diameter of 300 nm where 95% of the particles have a diameter within 10% of the average diameter, was formed from the tetraethoxyorthosilicate and 1-propanol.

A film of the mixture of silica, tin dioxide and palladium was applied to a glass substrate and heat treated at 400° C. for 2 hours. The film thickness was about 20 µm.

Figure 11:
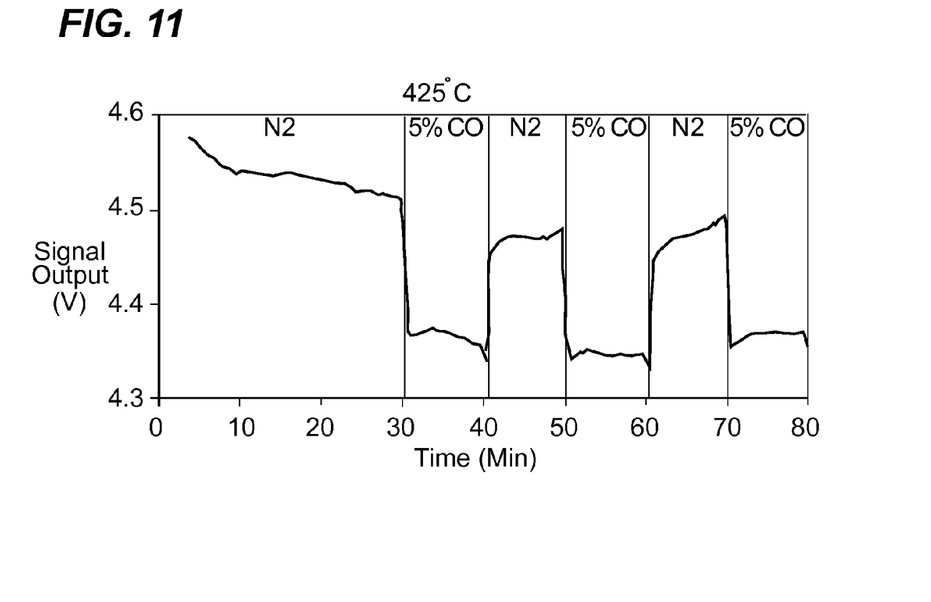
FIG. 11 is a graph showing the CO response optical reflection curve between alternating 5% CO in $N_2$ gas at 425° C. The graph is signal output in volts vs. time in minutes.
Figure 12:
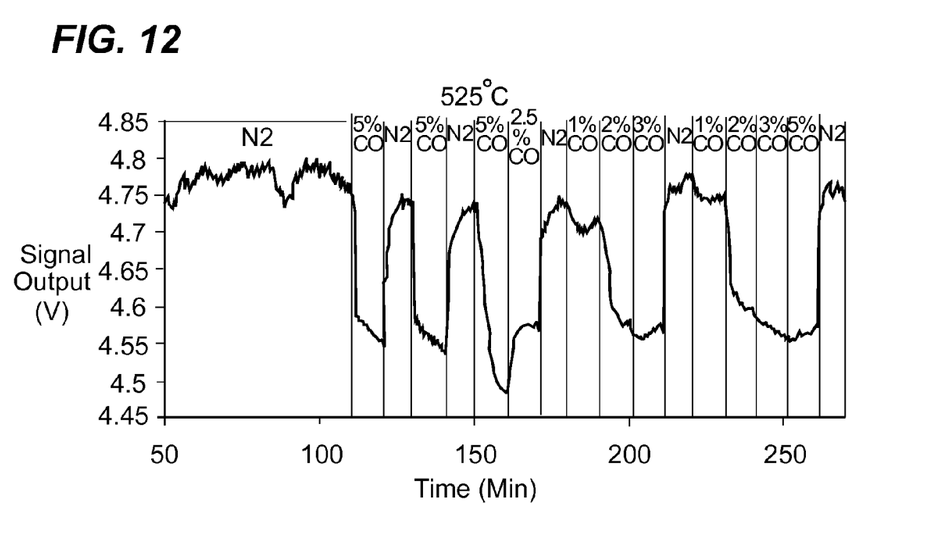
FIG. 12 is a graph showing the CO response optical reflection curve between alternating 5% CO in $N_2$ gas at 525° C. The graph is signal output in volts vs. time in minutes.

The fiber optic sensor was tested for carbon monoxide responses between 325° C. and 525° C. FIGS. 11 and 12 show the CO response optical reflection curve between alternating 5% CO in $N_2$ gas at 425° C. and 525° C., respectively. The sensor measured CO sensing across the temperature range.

Additional testing of 1%, 2% and 3% CO was performed at 525° C. Results showed that at 525° C., there were significant responses for CO gas. The signal level did change to the different CO concentrations.

Example 3

A mixture of 89.5 percent by weight tetraethoxyorthosilicate, 10.5 percent by weight palladium and 20 percent by weight based on the weight of the tetraethoxyorthosilicate and palladium of 1-propanol was prepared. A silica, having spherical particles with an average diameter of 300 nm where 95% of the particles have a diameter within 10% of the average diameter, was formed from the tetraethoxyorthosilicate and 1-propanol.

A film of the mixture of silica and palladium was applied to a glass substrate and heat treated at 500° C. for 2 hours. The film thickness was about 100 µm.

Figure 13:
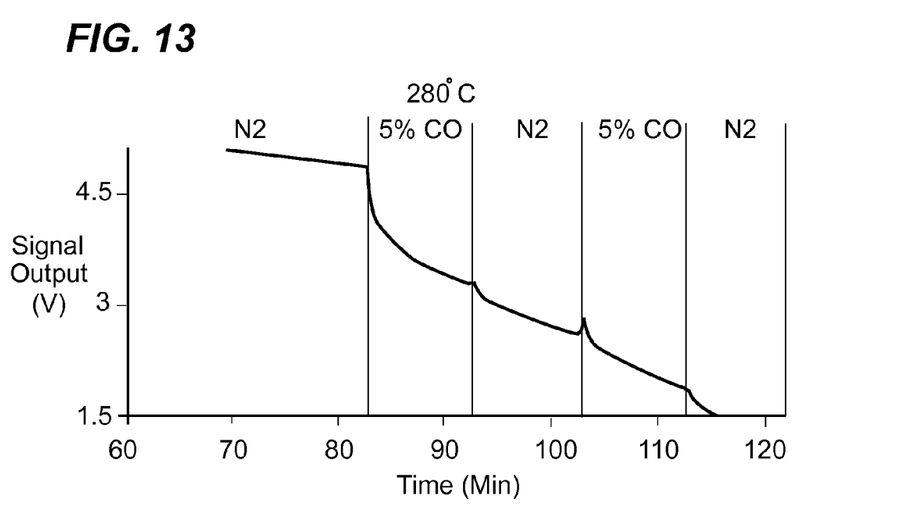
FIG. 13 is a graph showing the CO response optical reflection curve between alternating 5% CO in $N_2$ gas at 280° C. The graph is signal output in volts vs. time in minutes.
Figure 14:
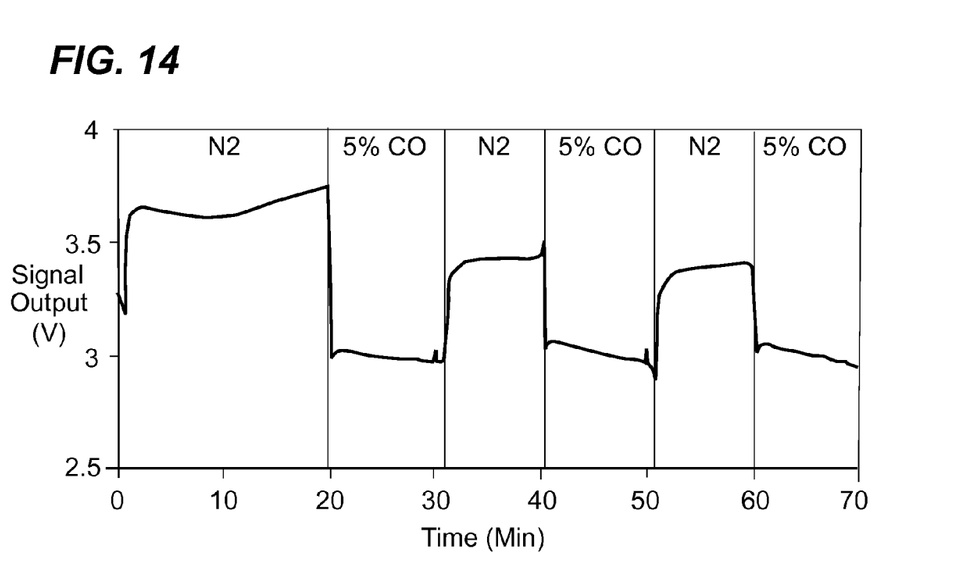
FIG. 14 is a graph showing the CO response optical reflection curve between alternating 5% CO in $N_2$ gas at 525° C. The graph is signal output in volts vs. time in minutes.

The fiber optic sensor was tested for carbon monoxide responses from room temperature to 525° C. There was no signal for CO measurement at room temperature, but there were good signal outputs for the high temperatures. FIGS. 13 and 14 show the CO response optical absorption curve between alternating 5% CO in $N_2$ gas at 280° C. and 525° C., respectively. As shown in FIG. 14, the response to the CO gas is quick and big.

While typical embodiments have been set forth for the purpose of illustration, the foregoing descriptions should not be deemed to be a limitation on the scope herein. Accordingly, various modifications, adaptations and alternatives may occur to one skilled in the art without departing from the spirit and scope herein.

Having described the Invention that which is claimed is:

1. A fiber optic sensor comprising a fiber having a cladding and a modified surface integral with the fiber said modified surface prepared by applying ceramic material to the fiber and comprising an open pore network and optical agents dispersed within the open pores of the open pore network wherein the modified surface is intimately bonded to the fiber surface, said optical agents comprise a Group 8-10 transition metal or a metal oxide selected from the group consisting of tin dioxide, yttrium oxide, vanadium oxide, titanium oxide and tungsten oxide and said modified surface is on the cladding.

2. The sensor of claim 1 wherein the ceramic material comprises a silica.

3. The sensor of claim 1 wherein the optical agents are transition metals selected from the group consisting of ruthenium, rhodium, platinum and palladium.

4. The sensor of claim 3 wherein the transition metal is palladium.

5. A process for making a fiber optic sensor comprising applying ceramic material to a fiber having a cladding and forming an open pore network structure, dispersing optical agents within the pores of the open pore network and integrating the ceramic material with the fiber, wherein said step of applying ceramic material consists of applying ceramic material to the cladding and said optical agents comprise a Group 8-10 transition metal or a metal oxide selected from the group consisting of tin dioxide, yttrium oxide, vanadium oxide, titanium oxide and tungsten oxide.

6. The process of claim 5 wherein the ceramic material is applied by coating the fiber cladding.

7. The process of claim 5 wherein the ceramic material is applied to the surface of the fiber cladding by forming a film.

8. The process of claim 5 wherein the fiber cladding surface is modified by coating the surface with a ceramic material.

9. The process of claim 5 wherein the fiber cladding surface is modified by dipping the surface into a solution comprising a ceramic material.

10. The process of claim 5 wherein said ceramic material comprises spherical particles.

11. The process of claim 5 wherein the ceramic material comprises a silica.

12. The process of claim 10 wherein the ceramic material is heat treated to form an open pore network and the modified fiber is dipped into a solution comprising optical agents, whereby the optical agents are dispersed within the pores of the open pore network.

13. The process of claim 5 wherein the optical agent is a transition metal or a metal oxide.

14. The process of claim 13 wherein the transition metal is palladium.

15. The process of claim 5 wherein the fiber is heat treated between about 300° C. and 600° C. for about 1 to about 4 hours.

16. A process for making a fiber optic sensor comprising applying a ceramic material mixture comprising ceramic material and optical agents to a fiber having a cladding, forming an open pore network structure within the ceramic material and integrating the ceramic material with the fiber, wherein said step of applying the ceramic material mixture consists of applying the ceramic material mixture to the cladding and said optical agents comprise a Group 8-10 transition metal or a metal oxide selected from the group consisting of tin dioxide, yttrium oxide, vanadium oxide, titanium oxide and tungsten oxide.

17. The process of claim 16 wherein the ceramic material mixture is applied by coating the fiber cladding.

18. The process of claim 16 wherein the ceramic material mixture is applied to the surface of the fiber cladding by forming a film.

19. The process of claim 16 wherein the fiber cladding surface is modified by dipping the surface into a solution comprising a ceramic material mixture.

20. The process of claim 16 wherein said ceramic material comprises spherical particles.

21. The process of claim 16 wherein the ceramic material comprises a silica.

22. The process of claim 16 wherein the optical agent is a transition metal or a metal oxide.

23. The process of claim 22 wherein the transition metal is palladium.

24. The process of claim 16 wherein the fiber is heat treated between about 300° C. and 600° C. for about 1 to about 4 hours.

25. The process of claim 16 wherein the ceramic material mixture further comprises a polymer.

26. The process of claim 25 wherein the polymer is an organic polymer.

27. A sensor prepared by the process of claim 14.

28. A sensor prepared by the process of claim 23.

* * * * *